United States Patent
Inoue et al.

(10) Patent No.: US 12,402,620 B2
(45) Date of Patent: Sep. 2, 2025

(54) CELL CRYOPRESERVATION PRETREATMENT OPERATION PLATE

(71) Applicant: Kitazato Corporation, Fuji (JP)

(72) Inventors: Futoshi Inoue, Fujinomiya (JP); Keiichi Kato, Tokyo (JP); Satoshi Ueno, Kawasaki (JP)

(73) Assignee: KITAZATO CORPORATION, Fuji (JP)

(*) Notice: Subject to any disclaimer, the term of this patent is extended or adjusted under 35 U.S.C. 154(b) by 863 days.

(21) Appl. No.: 17/592,785

(22) Filed: Feb. 4, 2022

(65) Prior Publication Data

US 2022/0151223 A1    May 19, 2022

Related U.S. Application Data

(63) Continuation of application No. PCT/JP2020/029814, filed on Aug. 4, 2020.

(30) Foreign Application Priority Data

Aug. 5, 2019   (JP) .................. 2019-143967

(51) Int. Cl.
*A01N 1/00*      (2006.01)
*A01N 1/125*    (2025.01)
(Continued)

(52) U.S. Cl.
CPC ............. *A01N 1/142* (2025.01); *A01N 1/125* (2025.01)

(58) Field of Classification Search
CPC ...................... A01N 1/0268; C12M 21/06
See application file for complete search history.

(56) References Cited

U.S. PATENT DOCUMENTS 10,494,593 B2 * 12/2019 Ejiri ................. C12M 23/08
2010/0221768 A1 * 9/2010 Akai ................. C12M 23/10
                                                          435/29
(Continued)

FOREIGN PATENT DOCUMENTS

JP    2000189155 A    7/2000
JP    2002315573 A    10/2002
(Continued)

OTHER PUBLICATIONS

International Preliminary Report/Written Opinion on Patentability (PCT/IB/338 and 373) issued in corresponding International Patent Application No. PCT/JP2020/029814 dated Feb. 17, 2022. (6 pages).

(Continued)

*Primary Examiner* — Nathan A Bowers
(74) *Attorney, Agent, or Firm* — BUCHANAN INGERSOLL & ROONEY PC

(57) ABSTRACT

A cell cryopreservation pretreatment operation plate includes a planar operation portion, a first recess for storing a treatment solution, a second recess for storing a treatment solution, a third recess for storing a treatment solution, and a fourth recess for storing discarded solutions. The planar operation portion includes, on a surface thereof, a first circular segment, second circular segment, and third circular segment for placing treatment solutions, an enlarged first circular segment enclosing the first circular segment, an enlarged second circular segment enclosing the second circular segment, and an enlarged third circular segment enclosing the third circular segment.

18 Claims, 7 Drawing Sheets

(51) Int. Cl.
*A01N 1/142* (2025.01)
*C12M 1/00* (2006.01)

(56) References Cited

U.S. PATENT DOCUMENTS

| | | | |
|---|---|---|---|
| 2010/0297600 A1 | 11/2010 | Cecchi | |
| 2011/0111447 A1* | 5/2011 | Ramsing | C12M 41/46 |
| | | | 435/303.1 |
| 2015/0329814 A1 | 11/2015 | Cecchi | |

FOREIGN PATENT DOCUMENTS

| | | | |
|---|---|---|---|
| JP | 2015053876 A | | 3/2015 |
| JP | 2016099547 A | | 5/2016 |
| JP | 2017060428 A | | 3/2017 |
| JP | 2017118884 A | | 7/2017 |
| JP | 6349847 B2 * | | 7/2018 |
| WO | 02085110 A1 | | 10/2002 |
| WO | 2016190322 A1 | | 12/2016 |

OTHER PUBLICATIONS

Katazato Corporation, "Kitazato Oocyte Cryo Plate", Feb. 13, 2019, [retrieved on Sep. 16, 2020] Internet URL:https://www.kitazato.co.jp/ja/pdf/cryo/Flyer-JPOocyte%20Cryo%20Plate20190213%20for%20mail.pdf. (2 pages) (cited in International Search Report and discussed in International Preliminary Report/Written Opinion).

Ueno, Satoshi et al. "Vitrification of human embryos and ovum-Freezing and thawing embryos and ovum by the Cryotop method-" J. Clin. Embryologist, 2017 (month unknown), pp. 130-133, vol. 19, No. 2, Medical Online. (4 pages) (cited in International Search Report and discussed in International Preliminary Report/Written Opinion).

The extended European Search Report issued Sep. 21, 2022, by the European Patent Office in corresponding European Patent Application No. 20850279.9-1111. (88 pages).

International Search Report (PCT/ISA/210) with translation and Written Opinion (PCT/ISA/237) mailed on Oct. 13, 2020, by the Japanese Patent Office as the International Searching Authority for International Application No. PCT/JP2020/029814. (10 pages).

* cited by examiner

CELL CRYOPRESERVATION PRETREATMENT OPERATION PLATE

TECHNICAL FIELD

The present invention relates to a cell cryopreservation pretreatment operation plate for use in cryopreservation of living cells including eggs such as mammalian ova and embryos, sperms, and stem cells such as hematopoietic stem cells and pluripotent stem cells.

BACKGROUND ART

Cryopreservation of mammalian embryos enables preservation of genetic resources of specific breeds and species. It is also effective for maintaining animal species that stand on the verge of extinction. In addition, it is also useful for treatment of human infertility.

As a method for cryopreserving mammalian embryos, JP 2000-189155A (Patent Document 1) has proposed a method in which mammalian embryos or ova are caused to adhere to the inner surface of a cryopreservation container, such as a frozen straw, frozen vial, or frozen tube that has been sterilized, using the least amount of a vitrification solution sufficient to encapsulate these embryos or ova, and thereafter, the cryopreservation container is hermetically sealed and then rapidly cooled by contact with liquid nitrogen.

The inventors of the present invention have proposed Patent Document 2 (JP 2002-315573A, WO 02/085110 A1). Patent Document 2 discloses an egg cryopreservation tool 1 including a main body 2 made of a cold-resistant material, an egg adhesion holding strip 3 attached to one end of the main body 2 and made of a material that is flexible, transparent, and resistant to liquid nitrogen, and a cylindrical member 4 detachably attached to the main body 2 in a manner capable of covering the egg adhesion holding strip 3, sealed at one end, and made of a cold-resistant material.

JP 2017-118884A (Patent Document 3) has proposed a cell treatment container for use in cell treatments using a treatment solution, including a treatment of embryos immediately before transfer.

CITATION LIST

Patent Documents

Patent Document 1: JP 2000-189155A
Patent Document 2: JP 2002-315573A (WO 02/085110 A1)
Patent Document 3: JP 2017-118884A (WO 2016/190322 A1)

SUMMARY OF INVENTION

Technical Problem

For the above-described egg cryopreservation, a vitrification preservation method is used. The vitrification preservation method is a technique utilizing the principle that the freezing point of an aqueous solution is lowered when it contains a cryoprotective agent such as glycerol or ethylene glycol, whereby the formation of ice crystals is inhibited even at temperatures below the freezing point. When this solution is rapidly cooled in liquid nitrogen, it can be solidified without forming ice crystals. Since water turns to a glassy solid without causing crystallization, this technique is called "vitrification". In order to freeze eggs using a vitrification method, the eggs need to be pretreated. The intended use of the treatment container of Patent Document 3 is not pretreatments for vitrification freezing but treatments such as a treatment of embryos immediately before transfer.

Containers dedicated to pretreatments for the above-described vitrification freezing have not been provided heretofore. Thus, at present, an ordinary petri dish, multi-well petri dish, center-well dish, and the like are used at each clinic with efforts to complete transfer operations in a short time while avoiding the occurrence of errors as much as possible.

It is an object of the present invention to provide a cell cryopreservation pretreatment operation plate that allows a pretreatment for vitrification freezing to be performed easily with few procedural errors.

Solution to Problem

The following is provided as means for achieving the above-described object.

A cell cryopreservation pretreatment operation plate comprising:
 a planar operation portion;
 a first recess for storing a low-concentration treatment solution that contains a cell membrane-permeable cryoprotectant at a low concentration;
 a second recess for storing a high-concentration treatment solution that contains a cell membrane-permeable cryoprotectant at a high concentration;
 a third recess for storing a high-concentration treatment solution that contains a cell membrane-permeable cryoprotectant at a high concentration; and
 a fourth recess for storing a discarded solution,
 wherein the planar operation portion includes, on a surface thereof, a first circular segment for placing a cell membrane-permeable cryoprotectant-free treatment solution, a second circular segment for placing the low-concentration treatment solution, and a third circular segment for placing the low-concentration treatment solution,
 the first circular segment, the second circular segment, and the third circular segment are located close to each other, and
 the planar operation portion further includes, on the surface thereof, an enlarged first circular segment enclosing the first circular segment, an enlarged second circular segment enclosing the second circular segment, and an enlarged third circular segment enclosing the third circular segment.

The following is provided as other means for achieving the above-described object.

A cell cryopreservation pretreatment operation plate comprising:
 a planar operation portion;
 a first recess for storing a cell treatment solution;
 a second recess for storing a cell treatment solution;
 a third recess for storing a cell treatment solution; and
 a fourth recess for storing a discarded solution,
 wherein the planar operation portion includes, on a surface thereof, a first circular segment for placing a cell treatment solution, a second circular segment for placing a cell treatment solution, and a third circular segment for placing a cell treatment solution,
 the first circular segment, the second circular segment, and the third circular segment are located close to each other, and the planar operation portion further includes, on the surface thereof, an enlarged first circular segment enclosing the first circular segment, an enlarged second circular segment enclosing the second circular segment, and an enlarged third circular segment enclosing the third circular segment.

DESCRIPTION OF EMBODIMENTS

Figure 1:
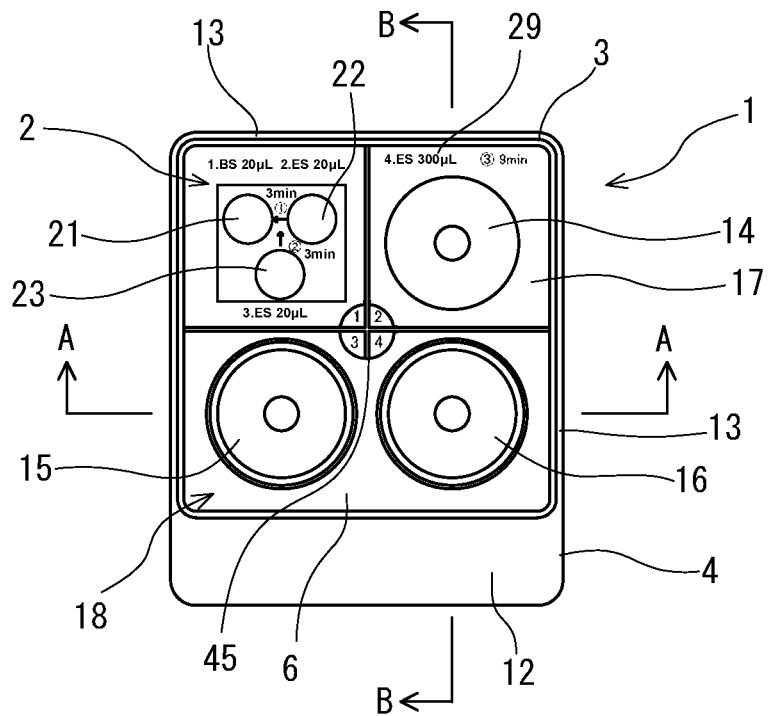
FIG. 1 is a front view of a cell cryopreservation pretreatment operation plate having the basic configuration of the cell cryopreservation pretreatment operation plate according to the present invention.
Figure 2:
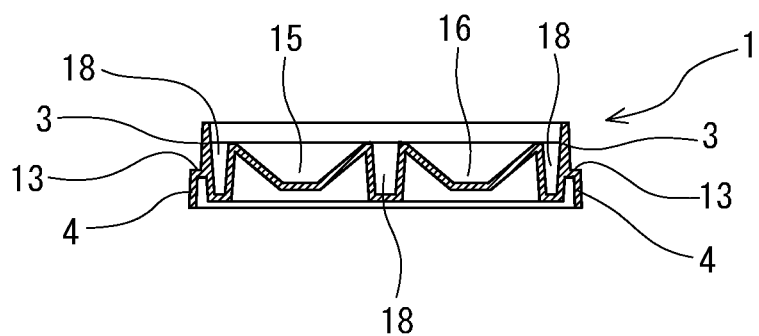
FIG. 2 is a cross-sectional view taken along line A-A in FIG. 1.

The cell cryopreservation pretreatment operation plate according to the present invention will be described with reference to examples illustrated in the drawings.

A cell cryopreservation pretreatment operation plate having the basic configuration of the cell cryopreservation pretreatment operation plate according to the present invention includes a planar operation portion 2, a first recess 14 for storing a low-concentration treatment solution that contains a cell membrane-permeable cryoprotectant at a low concentration, a second recess 15 for storing a high-concentration treatment solution that contains a cell membrane-permeable cryoprotectant at a high concentration, a third recess 16 for storing a high-concentration treatment solution that contains a cell membrane-permeable cryoprotectant at a high concentration, and a fourth recess 18 for storing discarded solutions (used treatment solutions). The planar operation portion 2 includes, on a surface thereof, a first circular segment 21 for placing a cell membrane-permeable cryoprotectant-free treatment solution, a second circular segment for placing the low-concentration treatment solution, and a third circular segment for placing the low-concentration treatment solution. The first circular segment 21, the second circular segment 22, and the third circular segment 23 are located close to each other.

Alternatively, the cell cryopreservation pretreatment operation plate having the basic configuration of the cell cryopreservation pretreatment operation plate according to the present invention may be as follows.

A cell cryopreservation pretreatment operation plate according to this embodiment includes a planar operation portion 2, a first recess 14 for storing a cell treatment solution, a second recess 15 for storing a cell treatment solution, a third recess 16 for storing a cell treatment solution, and a fourth recess 18 for storing discarded solutions. The planar operation portion 2 includes, on a surface thereof, a first circular segment 21 for placing a cell treatment solution, a second circular segment 22 for placing a cell treatment solution, and a third circular segment 23 for placing a cell treatment solution. The first circular segment 21, the second circular segment 22, and the third circular segment 23 are located close to each other.

Alternatively, the cell cryopreservation pretreatment operation plate having the basic configuration of the cell cryopreservation pretreatment operation plate according to the present invention may be as follows.

This cell cryopreservation pretreatment operation plate includes a planar operation portion 2, a first recess 14 for storing a treatment solution, a second recess 15 for storing a treatment solution, a third recess 16 for storing a treatment solution, and a fourth recess 18 for storing discarded solutions. The planar operation portion 2 includes, on a surface thereof, a first circular segment 21 for placing a treatment solution, a second circular segment 22 for placing a treatment solution, and a third circular segment 23 for placing a treatment solution. The first circular segment 21, the second circular segment 22, and the third circular segment 23 are located close to each other. The planar operation portion 2 further includes a first indication portion 26 in which the name and the amount of the treatment solution to be placed on the first circular segment 21 are indicated, a second indication portion 27 in which the name and the amount of the treatment solution to be placed on the second circular segment 22 are indicated, and a third indication portion 28 in which the name and the amount of the treatment solution to be placed on the third circular segment 23 are indicated. The cell cryopreservation pretreatment operation plate 1 further includes a fourth indication portion 29 in which the name and the amount of the treatment solution to be contained in the first recess 14 are indicated.

The cell cryopreservation pretreatment operation plate 1 shown in FIGS. 1 to 4 includes a lower surrounding wall 4, a surrounding side wall 3 extending upward from the lower surrounding wall 4, a bottom 6 located inside the surrounding side wall 3, and an upper surface portion 12 provided at one end portion of the lower surrounding wall 4. In the plate 1 of this example, the lower surrounding wall 4 is substantially rectangular and larger than the surrounding side wall 3, and on an upper surface of a portion of the lower surrounding wall 4 protruding from the surrounding side wall 3, the above-described upper surface portion 12, which is horizontally elongated, and a narrow U-shaped flat portion 13 that connects the lower end of both side portions and the back side portion of the surrounding side wall 3 to the upper end of the lower surrounding wall 4 are provided.

The lower surrounding wall 4 is a rectangular surrounding wall with curved corners. One end portion of the lower surrounding wall, specifically, the lower end portion (on the front side) in FIG. 1 of the lower surrounding wall has the upper surface portion 12 jointed to the upper end of the lower surrounding wall 4. The upper surface portion 12 is flat, and characters and the like can be written on the surface thereof with a writing tool. The upper surface portion 12 preferably has a rough surface, specifically a satin-finished surface. This makes writing on the surface with a writing tool or the like easier and also helps visual recognition of the written characters and the like.

Figure 3:
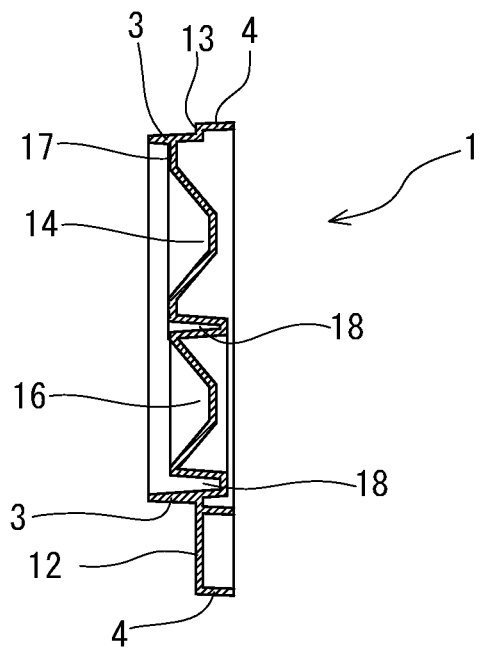
FIG. 3 is a cross-sectional view taken along line B-B in FIG. 1.

The cell cryopreservation pretreatment operation plate 1 has the surrounding side wall 3 extending upward from a portion of the lower surrounding wall 4 excluding the upper surface portion 12. Also, the narrow U-shaped flat portion 13 that connects the lower end of both side portions and the back side portion of the surrounding side wall 3 to the upper end of the lower surrounding wall 4 is provided. Thus, between the lower surrounding wall 4 and the surrounding side wall 3, a step is formed by the upper surface portion 12 and the flat portion 13. The upper surface of this step serves as a placement portion for a lid 5. As shown in FIG. 3, the surrounding side wall 3 is formed so as to be higher than the upper surface portion 12. In this example, as shown in FIGS. 1 to 4, the surrounding side wall 3 is a rectangular surrounding wall with curved corners.

Inside the surrounding side wall 3, a planar operation portion 2, a first recess 14 for storing a treatment solution, a second recess 15 for storing a treatment solution, a third recess 16 for storing a treatment solution, and a fourth recess 18 for storing discarded solutions are provided.

Figure 4:
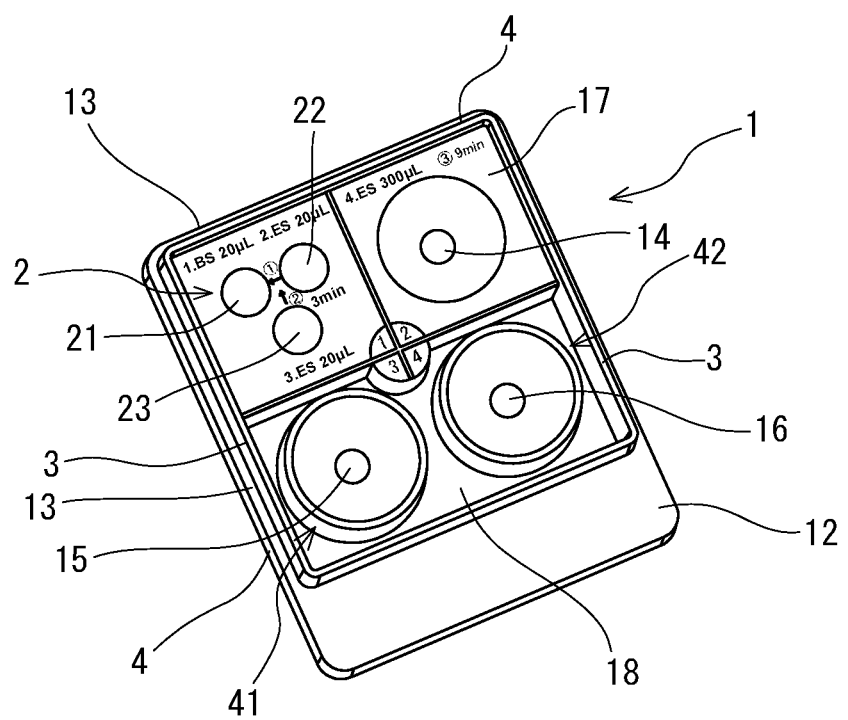
FIG. 4 is a perspective view of the cell cryopreservation pretreatment operation plate shown in FIG. 1.

As shown in FIG. 4, in this cell cryopreservation pretreatment operation plate 1, the planar operation portion 2 is provided at a position slightly lower than the upper end of the surrounding side wall 3 and is substantially rectangular. In this example, a second planar portion 17 is provided, and the first recess 14 is formed in the second planar portion 17. Specifically, the second planar portion 17 is provided adjacent to the planar operation portion 2, and the upper surface thereof is substantially level with the upper surface of the planar operation portion 2.

The first recess 14 is formed in the central portion of the second planar portion 17. The first recess 14 has a flat bottom surface in a small circular shape and a tapered side surface whose diameter decreases toward the bottom surface. Thus, the first recess 14 has an inverted truncated cone shape (the cross-sectional area thereof decreases toward the bottom surface). The first recess 14 is a recess for storing a cell treatment solution. Specifically, it is a recess for storing a low-concentration treatment solution that contains a cell membrane-permeable cryoprotectant at a low concentration.

As shown in FIGS. 1 to 4, this cell cryopreservation pretreatment operation plate 1 includes a first protruding portion 41 protruding upward from the bottom 6 inside the surrounding side wall 3, and the second recess 15 is formed in the first protruding portion 41. Further, the cell cryopreservation pretreatment operation plate 1 of this example includes a second protruding portion 42 protruding upward from the bottom 6 inside the surrounding side wall 3, and the third recess 16 is formed in the second protruding portion 42. The second recess 15 and the third recess 16 each have a flat bottom surface in a small circular shape and a tapered side surface whose diameter decreases toward the bottom surface. Thus, the second recess 15 and the third recess 16 each have an inverted truncated cone shape (the cross-sectional area thereof decreases toward the bottom surface).

The height of the surrounding side wall 3, in other words, the distance from the upper end of the surrounding side wall 3 to the planar operation portion 2, the second planar portion 17, the upper end of the first protruding portion 41 (the second recess 15), and the upper end of the second protruding portion 42 (the third recess 16) is preferably 1 to 5 mm and particularly preferably 1.5 to 4 mm.

The second recess 15 is a recess for storing a cell treatment solution, and specifically is a recess for storing a high-concentration treatment solution that contains a cell membrane-permeable cryoprotectant at a high concentration. Similarly, the third recess 16 is a recess for storing a cell treatment solution, and specifically is a recess for storing a high-concentration treatment solution that contains a cell membrane-permeable cryoprotectant at a high concentration. The concentration of the cell membrane-permeable cryoprotectant in the treatment solution to be stored in the second recess 15 may be different from the concentration of the cell membrane-permeable cryoprotectant in the treatment solution to be stored in the third recess 16.

As shown in FIGS. 1 to 4, this cell cryopreservation pretreatment operation plate 1 includes the fourth recess 18 for storing discarded solutions. Specifically, the fourth recess 18 is a recess formed by the side surfaces of the protruding portions 41 and 42, the inner surface of the surrounding side wall 3, and the bottom 6.

Figure 7:
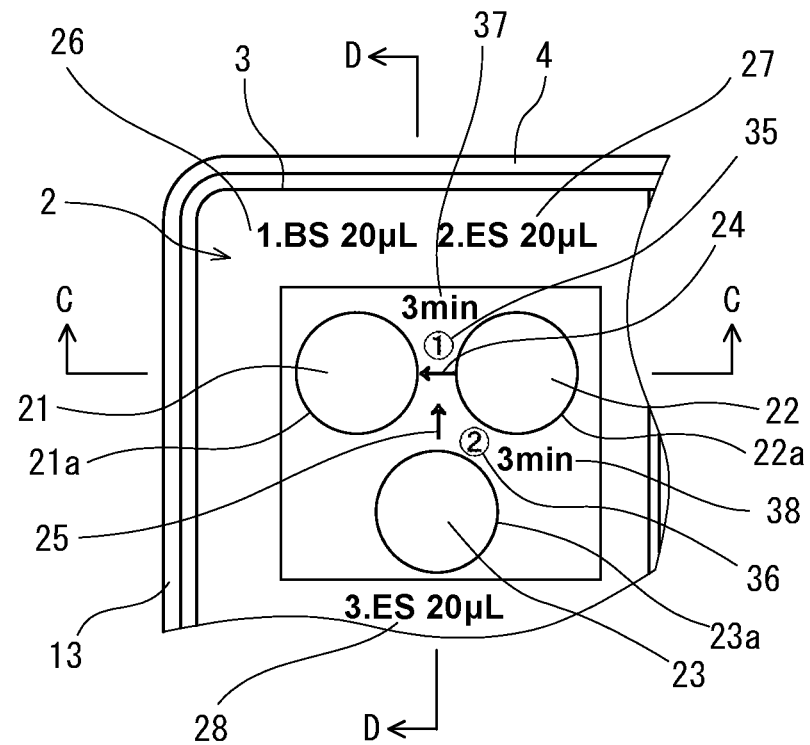
FIG. 7 is an enlarged view of a planar portion of the cell cryopreservation pretreatment operation plate shown in FIG. 1.

As shown in FIG. 7, the planar operation portion 2 includes, on a surface thereof, a first circular segment 21 for placing a treatment solution, a second circular portion 22 for placing a treatment solution, and a third circular segment 23 for placing a treatment solution.

The first circular segment 21 is a circular segment for placing a cell membrane-permeable cryoprotectant-free treatment solution. The second circular segment 22 is a circular segment for placing a treatment solution that contains a cell membrane-permeable cryoprotectant at a low concentration, and the third circular segment 23 is a circular segment for placing a treatment solution that contains a cell membrane-permeable cryoprotectant at a low concentration. The size (diameter) of each of the circular segments 21, 22, and 23 is preferably 3 to 8 mm and particularly preferably 4 to 7 mm. The area of each of the circular segments 21, 22, and 23 is preferably 7 to 50 mm$^2$ and particularly preferably 12 to 40 mm$^2$.

Although it is preferable that the circular segments 21, 22, and 23 have approximately the same size, their sizes may be different from each other. Also, each of the circular segments 21, 22, and 23 is preferably such that a predetermined amount of the treatment solution can be placed thereon. The amount of the treatment solution capable of being placed thereon is preferably 10 to 50 μL and particularly preferably 15 to 25 μL.

The first circular segment 21, the second circular segment 22, and the third circular segment 23 are located close to each other. The distance between the first circular segment 21 and the second circular segment 22 is preferably 1 to 5 mm and particularly preferably 1.5 to 3 mm. Preferably, as shown in FIG. 7, the third circular segment 23 is located close to the first circular segment 21 and the second circular segment 22 and is spaced apart from them by approximately the same distance. Specifically, as shown in FIG. 7, the third circular segment 23 is preferably located on the front side of the midpoint between the first circular segment 21 and the second circular segment 22. The distance between the third circular segment 23 and each of the first circular segment 21 and the second circular segment 22 is preferably 1 to 5 mm and particularly preferably 1.5 to 3 mm.

Figure 8:
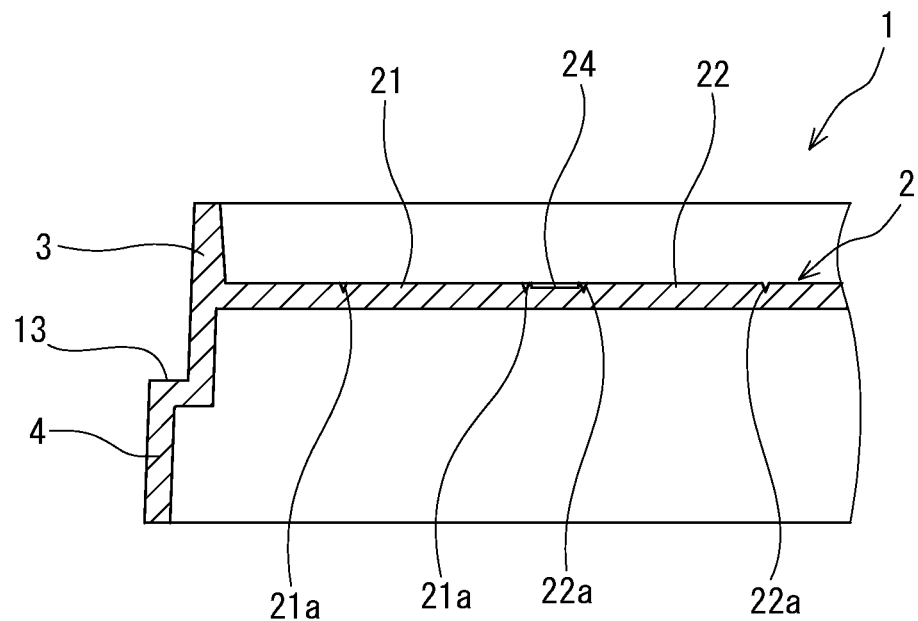
FIG. 8 is an enlarged cross-sectional view taken along line C-C in FIG. 7.
Figure 9:
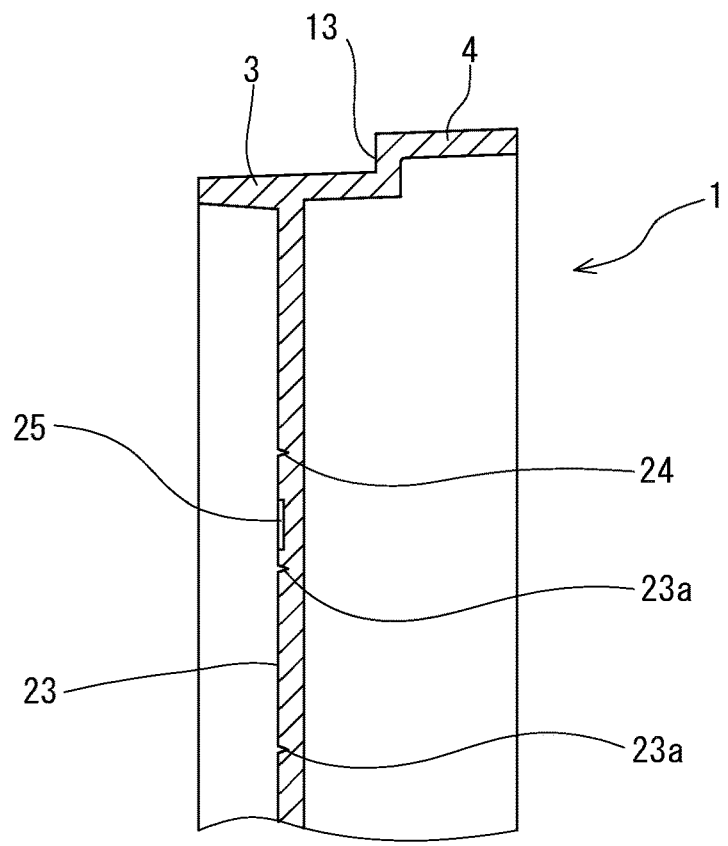
FIG. 9 is an enlarged cross-sectional view taken along line D-D in FIG. 7.

As shown in FIGS. 7 to 9, an outer edge 21a of the first circular segment 21, an outer edge 22a of the second circular segment 22, and an outer edge 23a of the third circular segment 23 are preferably annular grooves. Alternatively, the above-described outer edges 21a, 22a, and 23a may be annular ribs.

As shown in FIGS. 1 and 7, in this cell cryopreservation pretreatment operation plate 1, the planar operation portion 2 has a first indication portion 26 in which the name and the amount of the treatment solution to be placed on the first circular segment 21 are indicated. "BS" in the indication portion 26 is an abbreviation of "Basic Solution", which refers to a cell membrane-permeable cryoprotectant-free treatment solution. This is to inform an operator that the treatment solution to be placed on the first circular segment 21 is a cell membrane-permeable cryoprotectant-free treatment solution, and "20 µL" indicated beside "BS" is to inform an operator of the amount of the treatment solution to be placed.

As BS (cell membrane-permeable cryoprotectant-free treatment solution), those conventionally used are suitably used. As the cell membrane-permeable cryoprotectant-free treatment solution, it is suitable to use, for example, a basal cell culture medium (e.g., a cell culture medium containing HEPES [4-(2-HydroxyEthyl)-1-PiperazineEthaneSulfonic acid]) that does not contain a cell membrane-permeable cryoprotectant and contains compounds considered necessary, such as, for example: one type or two or more types of cell membrane-impermeable cryoprotectants selected from sucrose, trehalose, Percoll, polyethylene glycol, polyvinyl pyrrolidone, bovine serum albumin, Ficoll, and at least one type of water-soluble cellulose selected from the group consisting of hydroxypropyl cellulose, hydroxypropyl methylcellulose, and hydroxyethyl methylcellulose; and an antibiotic such as gentamicin.

As shown in FIGS. 1 and 7, this cell cryopreservation pretreatment operation plate 1 has a second indication portion 27 in which the name and the amount of the treatment solution to be placed on the second circular segment 22 are indicated. "ES" in the indication portion 27 is an abbreviation of "Equilibration Solution", which refers to a low-concentration treatment solution that contains a cell membrane-permeable cryoprotectant at a low concentration. This is to inform an operator that the treatment solution to be placed on the second circular segment 22 is a low-concentration treatment solution, and "20 µL" indicated beside "ES" is to inform an operator of the amount of the treatment solution to be placed.

As shown in FIGS. 1 and 7, this cell cryopreservation pretreatment operation plate 1 has a third indication portion 28 in which the name and the amount of the treatment solution to be placed on the third circular segment 23 are indicated. "ES" in the indication portion 28 is an abbreviation of "Equilibration Solution", which refers to a low-concentration treatment solution that contains a cell membrane-permeable cryoprotectant at a low concentration. This is to inform an operator that the treatment solution to be placed on the third circular segment 23 is a low-concentration treatment solution, and "20 µL" indicated beside "ES" is to inform an operator of the amount of the treatment solution to be placed.

As ES (low-concentration treatment solution that contains a cell membrane-permeable cryoprotectant at a low concentration), those conventionally used are suitably used. As the low-concentration treatment solution that contains a cell membrane-permeable cryoprotectant at a low concentration, it is suitable to use, for example, a basal cell culture medium (e.g., a cell culture medium containing HEPES [4-(2-HydroxyEthyl)-1-PiperazineEthaneSulfonic acid]) that contains a membrane-permeable cryoprotectant such as glycerol, propylene glycol, dimethylsulfoxide (DMSO), ethylene glycol, or butanediol at a low concentration and also contains a cell membrane-impermeable cryoprotectant such as sucrose, trehalose, Percoll, polyethylene glycol, polyvinyl pyrrolidone, bovine serum albumin, Ficoll, hydroxypropyl cellulose, hydroxypropyl methylcellulose, or hydroxyethyl methylcellulose. This ES also may contain an antibiotic such as gentamicin. The content of the cell membrane-permeable cryoprotectant in this ES is preferably 20% to 70% and particularly preferably 30% to 60% of the content of a cell membrane-permeable cryoprotectant in "VS" (high-concentration treatment solution that contains a cell membrane-permeable cryoprotectant at a high concentration) to be described below.

As shown in FIG. 1, this cell cryopreservation pretreatment operation plate 1 has a fourth indication portion 29 in which the name and the amount of the treatment solution to be stored in the first recess 14 are indicated. "ES" in the indication portion 29 is an abbreviation of "Equilibration Solution", which refers to a low-concentration treatment solution that contains a cell membrane-permeable cryoprotectant at a low concentration. This is to inform an operator that the treatment solution to be stored in (injected into) the first recess 14 is a low-concentration treatment solution, and "300 µL" indicated beside "ES" is to inform an operator of the amount of the treatment solution to be injected.

Figure 10:
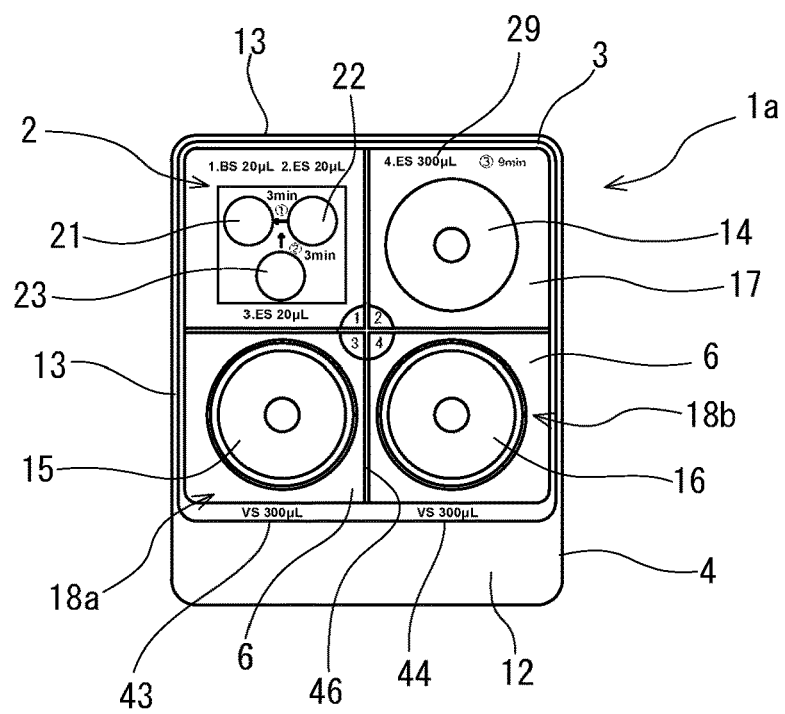
FIG. 10 is a front view of another example of the cell cryopreservation pretreatment operation plate having the basic configuration of the cell cryopreservation pretreatment operation plate according to the present invention.

Like a plate 1a shown in FIG. 10, the cell cryopreservation pretreatment operation plate may also have a fifth indication portion 43 in which the name and the amount of a treatment solution to be stored in the second recess 15 are indicated and a sixth indication portion 44 in which the name and the amount of a treatment solution to be stored in the third recess 16 are indicated.

Also, like the plate 1a shown in FIG. 10, the cell cryopreservation pretreatment operation plate may be configured such that the fourth recess is divided into a recess 18a on the second recess side and a recess 18b on the third recess side by a partition 46.

"VS" in each of the indication portions 43 and 44 is an abbreviation of "Vitrification Solution", which refers to a high-concentration treatment solution that contains a cell membrane-permeable cryoprotectant at a high concentration. This is to inform an operator that the treatment solution to be stored in (injected into) the second recess 15 and the third recess 16 is a high-concentration treatment solution, and "300 µL" indicated beside "VS" is to inform an operator of the amount of the treatment solution to be injected.

As VS (high-concentration treatment solution that contains a cell membrane-permeable cryoprotectant at a high concentration), those conventionally used are suitably used. As the high-concentration treatment solution that contains a cell membrane-permeable cryoprotectant at a high concentration, it is suitable to use, for example, a basal cell culture medium (e.g., a cell culture medium containing HEPES [4-(2-HydroxyEthyl)-1-PiperazineEthaneSulfonic acid]) that contains a cell membrane-permeable cryoprotectant such as glycerol, propylene glycol, dimethylsulfoxide (DMSO), ethylene glycol, or butanediol at a high concentration and also contains a cell membrane-impermeable cryoprotectant such as sucrose, trehalose, Percoll, polyethylene glycol, polyvinyl pyrrolidone, bovine serum albumin, Ficoll, hydroxypropyl cellulose, hydroxypropyl methylcellulose, or hydroxyethyl methylcellulose. This VS also may contain an antibiotic such as gentamicin. The content of the cell membrane-permeable cryoprotectant in this VS is preferably 1.5 to 3 times and particularly preferably 1.7 to 2.5 times the content of the cell membrane-permeable cryoprotectant in the above-described "ES" (low-concentration treatment solution that contains a cell membrane-permeable cryoprotectant at a low concentration).

As shown in FIGS. 1 and 7, in this cell cryopreservation pretreatment operation plate 1, the planar operation portion 2 includes, on the surface thereof, a first arrow indication 24 extending from the second circular segment 22 toward the first circular segment 21 and a second arrow indication 25 extending from the third circular segment 23 toward the first arrow indication 24. The second arrow indication 25 may extend toward the first circular segment 21.

In this cell cryopreservation pretreatment operation plate 1, as shown in FIGS. 1 and 7, the planar operation portion 2 includes, on the surface thereof, a first step order indication (1) near the first arrow indication and a second step order indication (2) near the second arrow indication. Also, as shown in FIG. 1, the second planar portion 17 includes a third step order indication (3). Further, the cell cryopreservation pretreatment operation plate 1 of this example includes a first step time indication near the first step order indication (1), a second step time indication near the second step order indication (2), and a third step time indication near the third step order indication (3).

As shown in FIGS. 1 and 4, in this cell cryopreservation pretreatment operation plate 1, the second planar portion 17 with the first recess 14 is located next to (on the right side of) the planar operation portion 2, and the second recess 15, the third recess 16, and the fourth recess 18 are located on the front side of the planar operation portion 2 and the second planar portion 17, whereby a rectangular operation surface is formed. The central portion of the rectangular operation surface includes an operation sequence indication 45 (1, 2, 3, 4) that indicates the order of operations to be performed in the planar operation portion 2, the first recess 14, the second recess 15, and the third recess 16, respectively. In the operation sequence indication, 3 and 4 are interchangeable.

Figure 5:
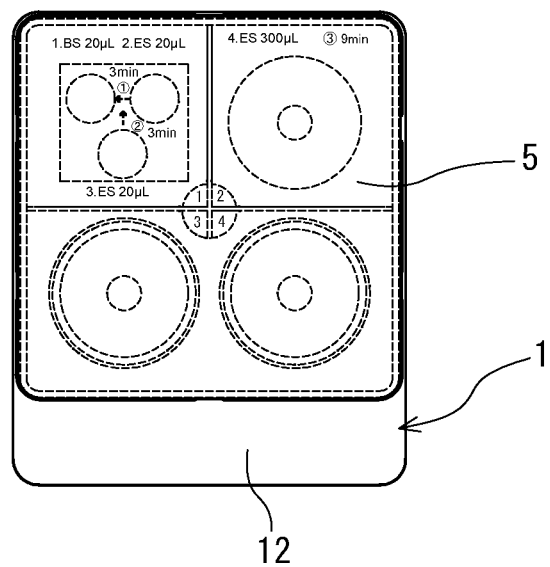
FIG. 5 is a front view of the cell cryopreservation pretreatment operation plate shown in FIG. 1 with a lid placed thereon.
Figure 6:
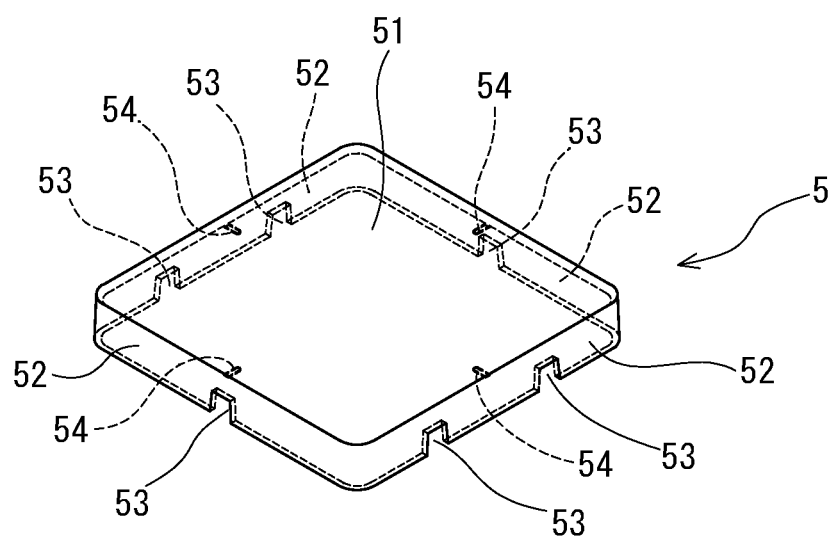
FIG. 6 is a perspective view of the lid placed on the cell cryopreservation pretreatment operation plate shown in FIG. 5.

As shown in FIGS. 5 and 6, the cell cryopreservation pretreatment operation plate preferably includes a lid 5 for covering the planar operation portion 2, the first recess 14, the second recess 15, and the third recess 16 at the same time. As shown in FIG. 6, the lid 5 in this example is configured to cover the above-described rectangular operation surface entirely, and the upper surface portion 12 is exposed in the state where the lid 5 is fitted onto the plate. Accordingly, the lid 5 does not interfere with operations such as writing characters on the upper surface portion 12. The lid 5 in this example has a top plate portion 51 and a surrounding side wall 52 extending downward from the top plate portion 51. The surrounding side wall 52 includes a plurality of sets of opposing slits 53 on its side surfaces. Further, opposing ribs 54 are provided on the inner upper surface of the lid 5.

The cell cryopreservation pretreatment operation plate 1 and the lid 5 are made of a synthetic resin material. The cell cryopreservation pretreatment operation plate 1 and the lid 5 desirably have high transparency, and accordingly, a transparent hard synthetic resin is suitably used. As the transparent hard synthetic resin, it is preferable to use a styrene resin such as polystyrene or SBS, polycarbonate, an acrylonitrile resin, polyolefin such as polypropylene or polyethylene, polyvinyl chloride, or a polyester resin such as PMMA (polymethyl methacrylate), polyethylene terephthalate, or polybutylene terephthalate.

Figure 11:
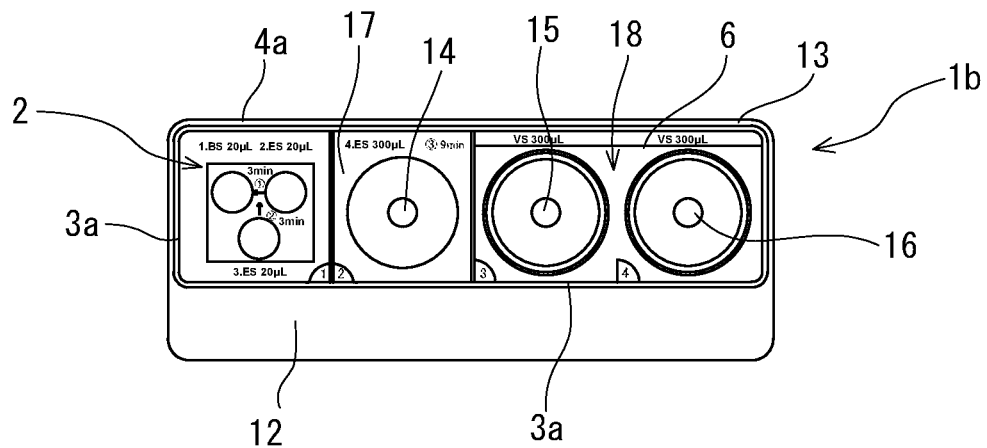
FIG. 11 is a front view of still another example of the cell cryopreservation pretreatment operation plate having the basic configuration of the cell cryopreservation pretreatment operation plate according to the present invention.

Next, a cell cryopreservation pretreatment operation plate 1b shown in FIG. 11 will be described. The basic configuration of this plate 1b is the same as that of the above-described plate 1. The differences between them are positions where a second recess 15, a third recess 16, and a fourth recess 18 are arranged relative to a planar operation portion 2 and a first recess 14.

In this cell cryopreservation pretreatment operation plate 1b, a second planar portion 17 with the first recess 14 is located next to (on the right side of) the planar operation portion 2, and the second recess 15, the third recess 16, and the fourth recess 18 are located next to (on the right side of) the second planar portion 17, whereby a horizontally elongated rectangular operation surface is formed. Accordingly, in the plate 1b, a lower surrounding wall 4a and a surrounding side wall 3a are also horizontally elongated rectangular, and an upper surface portion 12 is also horizontally elongated. The plate 1b also includes a narrow flat portion 13 that connects the lower end of both side portions and the back side portion of the surrounding side wall 3a to the upper end of the lower surrounding wall 4a. Further, this plate 1b also includes an operation sequence indication (1, 2, 3, 4) that indicates the order of operations to be performed in the planar operation portion 2, the first recess 14, the second recess 15, and the third recess 16, respectively.

Next, a cell cryopreservation pretreatment operation plate 1c according to an example of the present invention shown in FIG. 12 will be described. The basic configuration of this plate 1c is the same as that of the above-described plate 1. The differences between them are the configuration of a planar operation portion 2 and positions where the planar operation portion 2, a first recess 14, a second recess 15, a third recess 16, and a fourth recess 18 are arranged.

Figure 12:
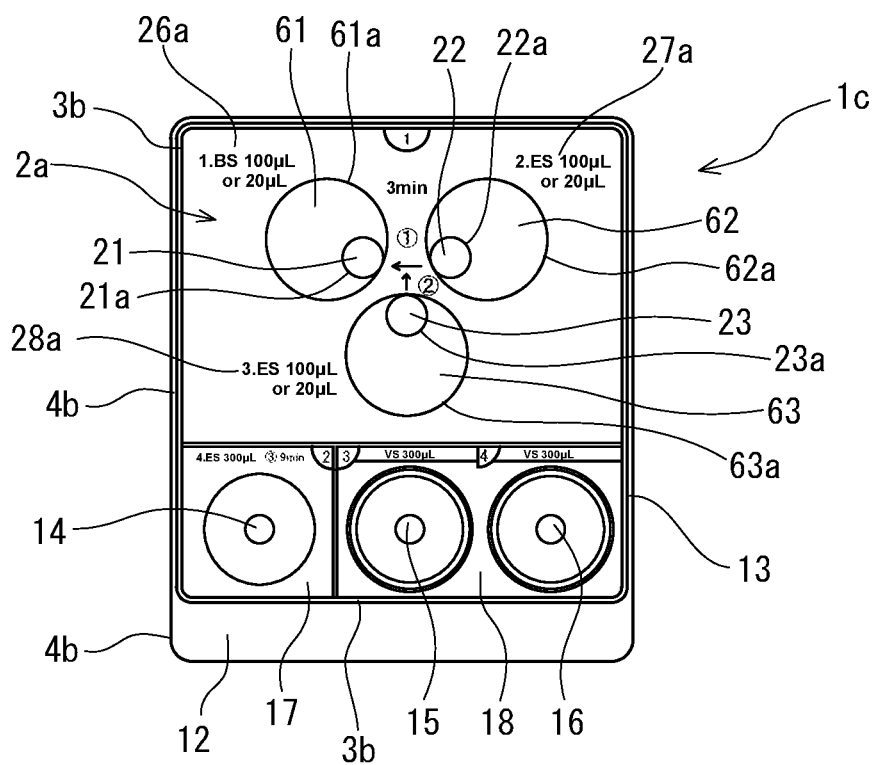
FIG. 12 is a front view of a cell cryopreservation pretreatment operation plate according to an example of the present invention.

As shown in FIG. 12, in the plate 1c of this example, the planar operation portion 2a is larger than the planar operation portion 2 of the above-described plate 1. The planar operation portion 2a includes, on a surface thereof, a first circular segment 21, a second circular segment 22, a third circular segment 23, an enlarged first circular segment 61 enclosing the first circular segment 21, an enlarged second circular segment 62 enclosing the second circular segment 22, and an enlarged third circular segment 63 enclosing the third circular segment 23. The sizes, arrangement, and the like of the first circular segment 21, the second circular segment 22, and the third circular segment 23 are the same as those in the above-described plate 1.

The enlarged first circular segment 61 has a larger diameter than the first circular segment 21, and encloses the first circular segment 21 in such a manner that the first circular segment 21 is located inside the enlarged first circular segment 61 and closer to or in contact with the outer edge of the enlarged first circular segment 61 rather than concentrically located in the enlarged first circular segment 61. Also, the enlarged second circular segment 62 has a larger diameter than the second circular segment 22, and encloses the second circular segment 22 in such a manner that the second circular segment 22 is located inside the enlarged second circular segment 62 and closer to or in contact with the outer edge of the enlarged second circular segment 62 rather than concentrically located in the enlarged second circular segment 62. Also, the enlarged third circular segment 63 has a larger diameter than the third circular segment 23, and encloses the third circular segment 23 in such a manner that the third circular segment 23 is located inside the enlarged third circular segment 63 and closer to or in contact with the outer edge of the enlarged third circular segment 63 rather than concentrically located in the enlarged third circular segment 63.

Outer edges 21a, 22a, 23a, 61a, 62a, and 63a of the first circular segment 21, the enlarged first circular segment 61, the second circular segment 22, the enlarged second circular segment 62, the third circular segment 23, and the enlarged third circular segment 63 are annular grooves. Alternatively, the above-described outer edges may be annular ribs.

The enlarged first circular segment 61 is a circular segment for placing a cell membrane-permeable cryoprotectant-free treatment solution. The enlarged second circular segment 62 is a circular segment for placing a treatment solution that contains a cell membrane-permeable cryoprotectant at a low concentration. The enlarged third circular segment 63 is a circular segment for placing a treatment solution that contains a cell membrane-permeable cryoprotectant at a low concentration. The diameters of the enlarged circular segments 61, 62, and 63 are preferably 1.5 to 3 times and particularly preferably 1.7 to 2.5 times the diameters of the circular segments 21, 22, and 23, respectively. Similarly, the areas of the enlarged circular segments 61, 62, and 63 are preferably 2 to 10 times and particularly preferably 3 to 7 times the areas of the circular segments 21, 22, and 23, respectively.

As shown in FIG. 12, in the cell cryopreservation pretreatment operation plate 1c of this example, the planar operation portion 2a includes a first indication portion 26a in which the name and the amounts (two amounts) of the treatment solution to be placed on the first circular segment 21 and the enlarged first circular segment 61 are indicated. "BS" in the indication portion 26a is an abbreviation of "Basic Solution", which refers to a cell membrane-permeable cryoprotectant-free treatment solution. "20 µL" indicated near "BS" is to inform an operator of the amount of the treatment solution to be placed on the first circular segment 21, and "100 µL" also indicated near "BS" is to inform an operator of the amount of the treatment solution to be placed on the enlarged first circular segment 61. The enlarged first circular segment 61 is used when treating a plurality of cells at the same time, and the first circular segment 21 is used when treating a single cell.

As shown in FIG. 12, in the cell cryopreservation pretreatment operation plate 1c of this example, the planar operation portion 2a includes a second indication portion 27a in which the name and the amounts (two amounts) of the treatment solution to be placed on the second circular segment 22 and the enlarged second circular segment 62 are indicated. "ES" in the indication portion 27a indicates a low-concentration treatment solution that contains a cell membrane-permeable cryoprotectant at a low concentration. "20 µL" indicated near "ES" is to inform an operator of the amount of the treatment solution to be placed on the second circular segment 22, and "100 µL" also indicated near "ES" is to inform an operator of the amount of the treatment solution to be placed on the enlarged second circular segment 62. The enlarged second circular segment 62 is used when treating a plurality of cells at the same time, and the second circular segment 22 is used when treating a single cell.

As shown in FIG. 12, in the cell cryopreservation pretreatment operation plate 1c of this example, the planar operation portion 2a includes a third indication portion 28a in which the name and the amounts (two amounts) of the treatment solution to be placed on the third circular segment 23 and the enlarged third circular segment 63 are indicated. "ES" in the indication portion 28a refers to a low-concentration treatment solution that contains a cell membrane-permeable cryoprotectant at a low concentration. "20 µL" indicated near "ES" is to inform an operator of the amount of the treatment solution to be placed on the third circular segment 23, and "100 µL" also indicated near "ES" is to inform an operator of the amount of the treatment solution to be placed on the enlarged third circular segment 63. The enlarged third circular segment 63 is used when treating a plurality of cells at the same time, and the third circular segment 23 is used when treating a single cell.

In the plate 1c of this example, the first recess 14, the second recess 15, the third recess 16, and the fourth recess 18 are arranged on the front side of the planar operation portion 2a. The plate 1c of this example also indicates the name and the amount of the treatment solution to be stored in (injected into) each of the first recess 14, the second recess 15, and the third recess 16. The planar operation portion 2, the first recess 14, the second recess 15, the third recess 16, and the fourth recess 18 are surrounded by a surrounding side wall 3b, and the upper surfaces of them are located slightly below the upper end of the surrounding side wall 3b. In the plate 1c of this example, a lower surrounding wall 4b is also substantially rectangular, and similarly to the plate 1, the lower surrounding wall 4b is larger than the surrounding side wall 3b, and on an upper surface of a portion of the lower surrounding wall 4b protruding from the surrounding side wall 3b, a horizontally elongated upper surface portion 12 and a narrow flat portion 13 that connects the lower end of both side portions and the back side portion of the surrounding side wall 3b to the upper end of the lower surrounding wall 4b are provided.

Figure 13:
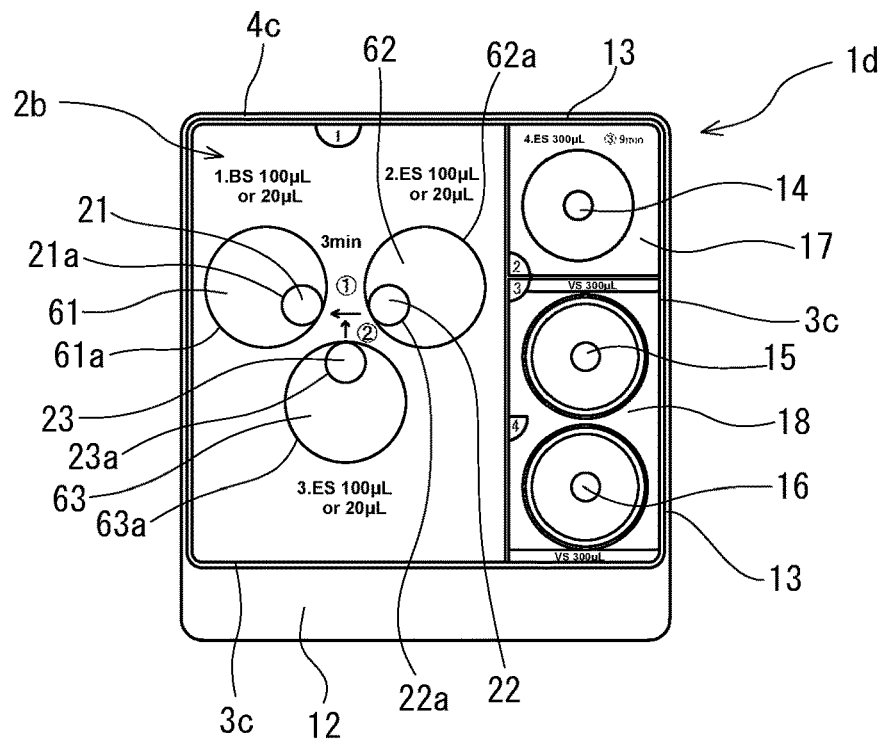
FIG. 13 is a front view of a cell cryopreservation pretreatment operation plate according to another example of the present invention.

Next, a cell cryopreservation pretreatment operation plate 1d of the example of the present invention shown in FIG. 13 will be described. The basic configuration of this plate 1d is the same as that of the above-described plate 1c. The differences between them are positions where a planar operation portion 2b, a first recess 14, a second recess 15, a third recess 16, and a fourth recess 18 are arranged.

In the plate 1d of this example, in a side portion (specifically, on the right side) of the planar operation portion 2b, the first recess 14, the second recess 15, and the third recess 16 are arranged in this order from the back side, and the fourth recess 18 is provided so as to surround the second recess 15 and the third recess 16. The plate 1d of this example also indicates the name and the amount of the treatment solution to be stored in (injected into) each of the first recess 14, the second recess 15, and the third recess 16. The planar operation portion 2b, the first recess 14, the second recess 15, the third recess 16, and the fourth recess 18 are surrounded by a surrounding side wall 3c, and the upper surfaces of them are located slightly below the upper end of the surrounding side wall 3c. In the plate 1d of this example, a lower surrounding wall 4c is also substantially rectangular, and similarly to the plate 1, the lower surrounding wall 4c is larger than the surrounding side wall 3c, and on an upper surface of a portion of the lower surrounding wall 4c protruding from the surrounding side wall 3c, a horizontally elongated upper surface portion 12 and a narrow flat portion 13 that connects the lower end of both side portions and the back side portion of the surrounding side wall 3c to the upper end of the lower surrounding wall 4c are provided.

Figure 14:
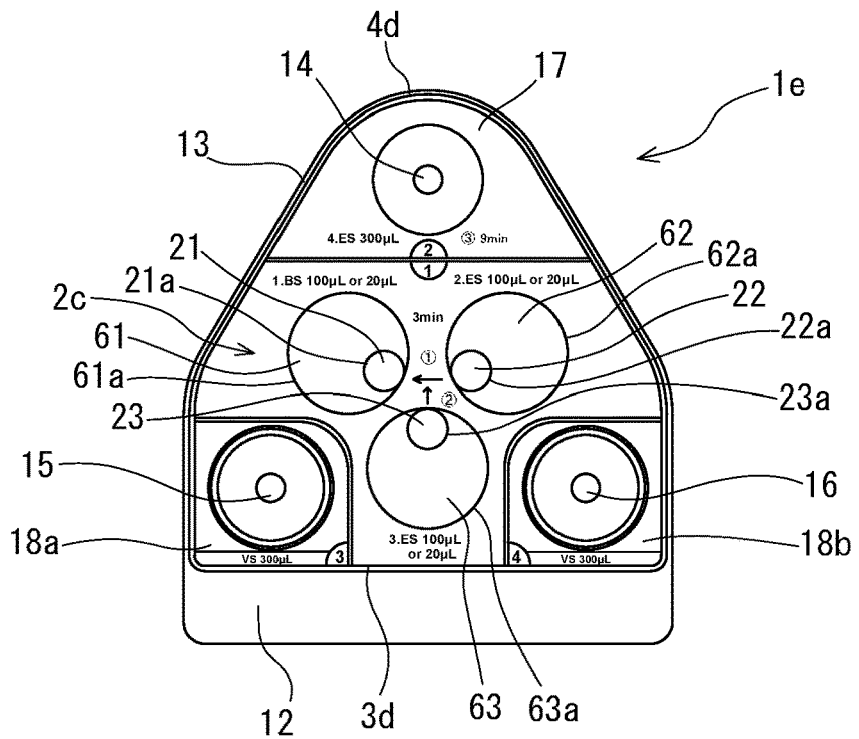
FIG. 14 is a front view of a cell cryopreservation pretreatment operation plate according to still another example of the present invention.

Next, a cell cryopreservation pretreatment operation plate 1e of the example of the present invention shown in FIG. 14 will be described. The basic configuration of this plate 1e is the same as that of the above-described plate 1c. The differences between them are positions where a planar operation portion 2c, a first recess 14, a second recess 15, a third recess 16, and fourth recesses 18a and 18b are arranged. In the plate 1e of this example, a lower surrounding wall 4d and a surrounding side wall 3d are each substantially pentagonal with the back side thereof being substantially triangular, and similarly to the plate 1, the lower surrounding wall 4d is larger than the surrounding side wall 3d, and on an upper surface of a portion of the lower surrounding wall 4d protruding from the surrounding side wall 3d, a horizontally elongated upper surface portion 12 and a narrow flat portion 13 that connects the lower end of both side portions and the back side portion of the surrounding side wall 3d to the upper end of the lower surrounding wall 4d are provided.

In the plate 1e of this example, the first recess 14 is arranged on the back side of the planar operation portion 2c. The second recess 15 and the fourth recess 18a are arranged in one (left) side portion on the front side of the planar operation portion 2c. The third recess 16 and the fourth recess 18b are arranged in the other (right) side portion on the front side of the planar operation portion 2c.

The plate 1e of this example also indicates the name and the amount of the treatment solution to be stored in (injected into) each of the first recess 14, the second recess 15, and the third recess 16. The planar operation portion 2c, the first recess 14, the second recess 15, the third recess 16, and the fourth recesses 18a and 18b are surrounded by the surrounding side wall 3d, and the upper surfaces of them are located slightly below the upper end of the surrounding side wall 3d.

Next, a cell cryopreservation pretreatment procedure using the cell cryopreservation pretreatment operation plate of the present invention will be described with reference to FIGS. 1 and 7.

First, a cell to be cryopreserved (e.g., an embryo), BS (cell membrane-permeable cryoprotectant-free treatment solution), ES (low-concentration treatment solution that contains a cell membrane-permeable cryoprotectant at a low concentration), and VS (high-concentration treatment solution that contains a cell membrane-permeable cryoprotectant at a high concentration) are prepared. Then, a predetermined amount (300 µL) of ES as indicated in the indication portion 29 is injected into the first recess 14 of the plate 1, predetermined amounts (300 µL) of VS are injected into the second recess 15 and the third recess 16, a proper amount (20 µL) of BS as indicated in the indication portion 26 is placed (dropped) on the first circular portion 21, a proper amount (20 µL) of ES as indicated in the indication portion 27 is placed (dropped) on the second circular portion 22, and a proper amount (20 µL) of ES as indicated in the indication portion 28 is placed (dropped) on the third circular portion 23. Preparation for the cell cryopreservation pretreatment is thus completed.

First, the cell to be cryopreserved is collected with a micropipette or the like, and transferred to the BS placed on the first circular segment 21. Subsequently, according to the indication (1) 35 and the arrow indication 24 in the planar operation portion 2 shown in FIG. 7, the second circular segment 22 and the first circular portion 21 are connected to each other using the member (e.g., pipette) used for the transfer. As a result, the second circular segment 22 and the first circular segment 21 are in communication with each other. Then, according to the indication in an indication portion 37, the cell is allowed to stand for 3 minutes. By this operation, the ES is gradually mixed with the BS containing the transferred cell in the first circular segment 21, thereby providing a mixed portion where the concentration of the low-concentration treatment solution in the treatment solution surrounding the cell has increased.

Subsequently, according to the indication (2) 36 and the arrow indication 25 in the planar operation portion 2 shown in FIG. 7, the third circular segment 23 is connected to the above-described mixed portion using the member (e.g., pipette) used for the transfer. As a result, the second circular segment 22, the first circular segment 21, and the third circular segment 23 are in communication with each other. Then, according to the indication in an indication portion 38, the cell is allowed to stand for 3 minutes. By this operation, the concentration of the low-concentration treatment solution in the treatment solution surrounding the cell to be cryopreserved increases further and gradually. This allows a gradual increase in the concentration of the cell membrane-permeable cryoprotectant in the treatment solution surrounding the cells to be cryopreserved, thereby allowing an equilibration treatment of the cell to be cryopreserved to proceed without damaging the cell. Through the above-described operations, the first step of equilibration is completed.

In particular, the plate 1 of this example is configured such that the planar operation portion 2 includes, on the surface thereof, the first circular segment 21 for placing a cell membrane-permeable cryoprotectant-free treatment solution, the second circular segment 22 for placing a low-concentration treatment solution, and the third circular segment 23 for placing a low-concentration treatment solution, and the first circular segment, the second circular segment, and the third circular segment are located close to each other. With this configuration, the above-described preparation for the equilibration and also operations for the equilibration can be carried out easily and reliably.

The cell having undergone the first step of the equilibration on the planar operation portion 2 in the above-described manner is then aspirated with the micropipette or the like, and placed on the surface of the ES injected in the first recess 14. Thereafter, the cell is allowed to stand for 9 minutes. When the cell placed on the surface of the ES is an embryo, it can be observed that the embryo shrinks while sinking within 30 seconds, and the operator waits for full recovery of the volume of the embryo that has once shrunk largely. The second step of equilibration is thus completed.

Subsequently, the cell in the first recess 14 is aspirated with the micropipette or the like and then placed on the surface of the second recess 15 storing the VS injected thereto. In this operation, the amount of the ES solution brought to the VS solution in the second recess 15 should be made as small as possible. After placing the cell, the ES remaining in the micropipette is discarded in the fourth recess 18 for storing discarded solutions. Subsequently, the micropipette is rinsed with the VS in the second recess 15 by aspirating fresh VS from the edge of the second recess 15 and then discarding the VS. In the second recess 15 (VS), sufficient pipetting (vigorously expelling the embryo from the pipette into the VS and then quickly stirring the solution around the embryo several times) is performed while changing the position such that the pipetting is performed at about three different sites. The cell is subjected to replacement of extracellular ES with the VS in the second recess 15 until shimmering due to the presence of the ES is no longer visible. The third step of equilibration is thus completed.

Subsequently, the VS in the micropipette is discarded in the fourth recess 18 for storing discarded solutions, and fresh VS injected in the third recess 16 is aspirated. Then, the cell in the second recess 15 is aspirated with the micropipette containing the aspirated fresh VS, and the cell is introduced into the third recess 16 storing the VS injected therein. Sufficient pipetting (vigorously expelling the embryo from the pipette into the VS and then quickly stirring the solution around the embryo several times) is performed while changing the position such that the pipetting is performed at about two different sites. Then, the operator checks whether the cell has shrunk to be flat in shape owing to dehydration. The equilibration is thus completed.

Subsequently, the cell to be cryopreserved is collected at the tip of the micropipette, and under a microscope, the cell and a small amount of VS are placed on a living cell holding portion (not shown) of a living cell cryopreservation tool (not shown). The living cell holding portion with the cell of the living cell cryopreservation tool is immersed in liquid nitrogen prepared beforehand to freeze (vitrify) the cell. Then, the living cell cryopreservation tool with the cell is inserted into a cylindrical member (not shown), and this cylindrical housing member with the living cell cryopreservation tool contained therein is then stored in a storage container (not shown). Subsequently, the storage container is placed in a liquid nitrogen tank for storage.

INDUSTRIAL APPLICABILITY

The cell cryopreservation pretreatment operation plate of the present invention is as described below.
(1) A cell cryopreservation pretreatment operation plate comprising:
   a planar operation portion;
   a first recess for storing a low-concentration treatment solution that contains a cell membrane-permeable cryoprotectant at a low concentration;
   a second recess for storing a high-concentration treatment solution that contains a cell membrane-permeable cryoprotectant at a high concentration;
   a third recess for storing a high-concentration treatment solution that contains a cell membrane-permeable cryoprotectant at a high concentration; and
   a fourth recess for storing a discarded solution,
   wherein the planar operation portion includes, on a surface thereof, a first circular segment for placing a cell membrane-permeable cryoprotectant-free treatment solution, a second circular segment for placing the low-concentration treatment solution, and a third circular segment for placing the low-concentration treatment solution,
   the first circular segment, the second circular segment, and the third circular segment are located close to each other, and
   the planar operation portion further includes, on the surface thereof, an enlarged first circular segment enclosing the first circular segment, an enlarged second circular segment enclosing the second circular segment, and an enlarged third circular segment enclosing the third circular segment.

In this plate, a proper amount of a cell membrane-permeable cryoprotectant-free treatment solution is placed (dropped) on the first circular segment, a proper amount of a low-concentration treatment solution is placed (dropped) on the second circular segment, and a proper amount of a low-concentration treatment solution is placed (dropped) on the third circular segment. The cell to be cryopreserved is then transferred to the cell membrane-permeable cryoprotectant-free treatment solution, and subsequently, the second circular segment and the first circular segment are connected to each other using the member (e.g., pipette) used for the transfer. As a result, the low-concentration treatment solution is gradually mixed with the cell membrane-permeable cryoprotectant-free treatment solution, whereby the concentration of the low-concentration treatment solution in the treatment solution surrounding the cell to be cryopreserved increases. Further, by connecting, with the member (e.g., pipette) used for the transfer, the third circular segment to the above-described mixed portion where the cell membrane-permeable cryoprotectant-free treatment solution and the low-concentration treatment solution are mixed together, the low-concentration treatment solution is gradually mixed with the mixed portion, whereby the concentration of the low-concentration treatment solution in the treatment solution surrounding the cell to be cryopreserved increases gradually. This allows a gradual increase in the concentration of the cell membrane-permeable cryoprotectant in the treatment solution surrounding the cell to be cryopreserved, whereby an equilibration treatment of the cell with the cell membrane-permeable cryoprotectant can be carried out favorably.

In particular, the above-described preparation for equilibration and also a favorable equilibration treatment can be carried out easily and reliably with the configuration in which the planar operation portion includes, on the surface thereof, the first circular segment for placing a cell membrane-permeable cryoprotectant-free treatment solution, the second circular segment for placing a low-concentration treatment solution, and the third circular segment for placing a low-concentration treatment solution, and the first circular segment, the second circular segment, and the third circular segment are located close to each other.

The enlarged circular segments are used when treating a plurality of cells at the same time, and the smaller circular segments inside the enlarged circular segments are used when treating a single cell. Thus, the circular segments and the enlarged circular segments can be used appropriately depending on the number of cells to be treated.

Embodiments of the above-described cell cryopreservation pretreatment operation plate are as described below.
(2) The cell cryopreservation pretreatment operation plate according to above (1),
   wherein the planar operation portion includes a first indication portion in which a name and an amount of a treatment solution to be placed on the first circular segment are indicated, a second indication portion in which a name and an amount of a treatment solution to be placed on the second circular segment are indicated, and a third indication portion in which a name and an amount of a treatment solution to be placed on the third circular segment are indicated.
(3) The cell cryopreservation pretreatment operation plate according to above (1) or (2), further comprising a fourth indication portion in which the name and the amount of the treatment solution to be contained in the first recess are indicated.
(4) The cell cryopreservation pretreatment operation plate according to any one of above (1) to (3),
   wherein the planar operation portion includes, on the surface thereof, a first arrow indication extending from the second circular segment toward the first circular segment and a second arrow indication extending from the third circular segment toward the first arrow indication or toward the first circular segment.
(5) The cell cryopreservation pretreatment operation plate according to any one of above (1) to (4), further comprising a lid for covering the planar operation portion, the first recess, the second recess, and the third recess at the same time.

(6) The cell cryopreservation pretreatment operation plate according to any one of above (1) to (5), further comprising a bottom, a surrounding side wall extending upward from the bottom, and a protruding portion extending upward from the bottom,
- wherein the second recess or the third recess is provided in the protruding portion, and
- the fourth recess is formed by a side surface of the protruding portion, an inner surface of the surrounding side wall, and the bottom.

(7) The cell cryopreservation pretreatment operation plate according to any one of above (1) to (6), further comprising a bottom, a surrounding side wall extending upward from the bottom, a first protruding portion protruding upward from the bottom, and a second protruding portion protruding upward from the bottom,
- wherein the second recess is provided in the first protruding portion,
- the third recess is provided in the second protruding portion, and
- the fourth recess is formed by side surfaces of the protruding portions, an inner surface of the surrounding side wall, and the bottom.

(8) The cell cryopreservation pretreatment operation plate according to any one of above (1) to (7), further comprising a second planar portion,
- wherein the first recess is formed in the second planar portion.

(9) The cell cryopreservation pretreatment operation plate according to any one of above (1) to (8),
- wherein the planar operation portion includes a first indication portion in which the name and the amounts of the treatment solution to be placed on the first circular segment and the enlarged first circular segment are indicated, a second indication portion in which the name and the amounts of the treatment solution to be placed on the second circular segment and the enlarged second circular segment are indicated, and a third indication portion in which the name and the amounts of the treatment solution to be placed on the third circular segment and the enlarged third circular segment are indicated.

Also, the cell cryopreservation pretreatment operation plate of the present invention is as described below.

(10) A cell cryopreservation pretreatment operation plate comprising:
- a planar operation portion;
- a first recess for storing a cell treatment solution;
- a second recess for storing a cell treatment solution;
- a third recess for storing a cell treatment solution; and
- a fourth recess for storing a discarded solution,
- wherein the planar operation portion includes, on a surface thereof, a first circular segment for placing a cell treatment solution, a second circular segment for placing a cell treatment solution, and a third circular segment for placing a cell treatment solution,
- the first circular segment, the second circular segment, and the third circular segment are located close to each other, and
- the planar operation portion further includes, on the surface thereof, an enlarged first circular segment enclosing the first circular segment, an enlarged second circular segment enclosing the second circular segment, and an enlarged third circular segment enclosing the third circular segment.

Embodiments of the above-described cell cryopreservation pretreatment operation plate are as described below.

(11) The cell cryopreservation pretreatment operation plate according to above (10),
- wherein the planar operation portion includes a first indication portion in which a name and an amount of a cell treatment solution to be placed on the first circular segment are indicated, a second indication portion in which a name and an amount of a cell treatment solution to be placed on the second circular segment are indicated, and a third indication portion in which a name and an amount of a cell treatment solution to be placed on the third circular segment are indicated, and
- the cell cryopreservation pretreatment operation plate further includes a fourth indication portion in which the name and the amount of the cell treatment solution to be contained in the first recess are indicated.

(12) The cell cryopreservation pretreatment operation plate according to above (10) or (11), wherein
- the planar operation portion includes a first indication portion in which the name and the amounts of the cell treatment solution to be placed on the first circular segment and the enlarged first circular segment are indicated, a second indication portion in which the name and the amounts of the cell treatment solution to be placed on the second circular segment and the enlarged second circular segment are indicated, and a third indication portion in which the name and the amounts of the cell treatment solution to be placed on the third circular segment and the enlarged third circular segment are indicated.

(13) The cell cryopreservation pretreatment operation plate according to any one of above (10) to (12),
- wherein the planar operation portion includes, on the surface thereof, a first arrow indication extending from the second circular segment toward the first circular segment and a second arrow indication extending from the third circular segment toward the first arrow indication or toward the first circular segment.

The invention claimed is:

1. A cell cryopreservation pretreatment operation plate comprising:
- a planar operation portion;
- a first recess for storing a low-concentration treatment solution that contains a cell membrane-permeable cryoprotectant at a low concentration;
- a second recess for storing a high-concentration treatment solution that contains a cell membrane-permeable cryoprotectant at a high concentration;
- a third recess for storing a high-concentration treatment solution that contains a cell membrane-permeable cryoprotectant at a high concentration; and
- a fourth recess for storing a discarded solution,
- wherein the planar operation portion includes, on a surface thereof, a first circular segment for placing a cell membrane-permeable cryoprotectant-free treatment solution, a second circular segment for placing the low-concentration treatment solution, and a third circular segment for placing the low-concentration treatment solution,
- the planar operation portion further includes, on the surface thereof, an enlarged first circular segment for placing a cell membrane-permeable cryoprotectant-free treatment solution, an enlarged second circular segment for placing the low-concentration treatment solution, and an enlarged third circular segment for placing the low-concentration treatment solution, the enlarged first circular segment enclosing the first circular segment, the enlarged second circular segment enclosing the second circular segment, and the enlarged third circular segment enclosing the third circular segment, the enlarged first circular segment has a diameter larger than a diameter of the first circular segment and encloses the first circular segment in such a manner that the first circular segment is located inside the enlarged first circular segment and is in contact with an outer edge of the enlarged first circular segment, the enlarged second circular segment has a diameter larger than a diameter of the second circular segment and encloses the second circular segment in such a manner that the second circular segment is located inside the enlarged second circular segment and is in contact with an outer edge of the enlarged second circular segment, the enlarged third circular segment has a diameter larger than a diameter of the third circular segment and encloses the third circular segment in such a manner that the third circular segment is located inside the enlarged third circular segment and is in contact with an outer edge of the enlarged third circular segment, outer edges of the first circular segment, the second circular segment and the third circular segment are annular grooves, outer edges of the enlarged first circular segment, the enlarged second circular segment and the enlarged third circular segment are annular grooves, the diameter of the enlarged first circular segment is 1.5 to 3 times the diameter of the first circular segment, and an area of the enlarged first circular segment is 2 to 10 times an area of the first circular segment, the diameter of the enlarged second circular segment is 1.5 to 3 times the diameter of the second circular segment, and an area of the enlarged second circular segment is 2 to 10 times an area of the second circular segment, and the diameter of the enlarged third circular segment is 1.5 to 3 times the diameter of the third circular segment, and an area of the enlarged third circular segment 3 is 2 to 10 times an area of the third circular segment.

2. The cell cryopreservation pretreatment operation plate according to claim 1,
wherein the planar operation portion includes a first indication portion in which a name and an amount of a treatment solution to be placed on the first circular segment are indicated, a second indication portion in which a name and an amount of a treatment solution to be placed on the second circular segment are indicated, and a third indication portion in which a name and an amount of a treatment solution to be placed on the third circular segment are indicated.

3. The cell cryopreservation pretreatment operation plate according to claim 2, further comprising a fourth indication portion in which the name and the amount of the treatment solution to be contained in the first recess are indicated.

4. The cell cryopreservation pretreatment operation plate according to claim 1,
wherein the planar operation portion includes, on the surface thereof, a first arrow indication extending from the second circular segment toward the first circular segment and a second arrow indication extending from the third circular segment toward the first arrow indication or toward the first circular segment.

5. The cell cryopreservation pretreatment operation plate according to claim 1, further comprising a lid for covering the planar operation portion, the first recess, the second recess, and the third recess at the same time.

6. The cell cryopreservation pretreatment operation plate according to claim 1, further comprising a bottom, a surrounding side wall extending upward from the bottom, and a protruding portion extending upward from the bottom,
wherein the second recess or the third recess is provided in the protruding portion, and
the fourth recess is formed by a side surface of the protruding portion, an inner surface of the surrounding side wall, and the bottom.

7. The cell cryopreservation pretreatment operation plate according to claim 1, further comprising a bottom, a surrounding side wall extending upward from the bottom, a first protruding portion protruding upward from the bottom, and a second protruding portion protruding upward from the bottom,
wherein the second recess is provided in the first protruding portion,
the third recess is provided in the second protruding portion, and
the fourth recess is formed by side surfaces of the protruding portions, an inner surface of the surrounding side wall, and the bottom.

8. The cell cryopreservation pretreatment operation plate according to claim 1, further comprising a second planar portion,
wherein the first recess is formed in the second planar portion.

9. The cell cryopreservation pretreatment operation plate according to claim 1,
wherein the planar operation portion includes a first indication portion in which the name and the amounts of the treatment solution to be placed on the first circular segment and the enlarged first circular segment are indicated, a second indication portion in which the name and the amounts of the treatment solution to be placed on the second circular segment and the enlarged second circular segment are indicated, and a third indication portion in which the name and the amounts of the treatment solution to be placed on the third circular segment and the enlarged third circular segment are indicated.

10. The cell cryopreservation pretreatment operation plate according to claim 1,
wherein the first circular segment, the second circular segment and the third circular segment each have a respective center,
wherein the enlarged first circular segment, the enlarged second circular segment and the enlarged third circular segment each have a respective center,
wherein a first imaginary triangle connects the center of the first circular segment, the center of the second circular segment and the center of the third circular segment to each other such that a first corner of the first imaginary triangle is coincident with the center of the first circular segment, a second corner of the first imaginary triangle is coincident with the center of the second circular segment and a third corner of the first imaginary triangle is coincident with the center of the third circular segment,
wherein a second imaginary triangle connects the center of the enlarged first circular segment, the center of the second circular segment and the center of the enlarged third circular segment to each other such that a first corner of the second imaginary triangle is coincident with the center of the enlarged first circular segment, a second corner of the second imaginary triangle is coincident with the center of the enlarged second circular segment and a third corner of the second imaginary triangle is coincident with the center of the enlarged third circular segment, and wherein a size of the first imaginary triangle and a size of the second imaginary triangle are different.

11. The cell cryopreservation pretreatment operation plate according to claim 1, wherein the size of the first imaginary triangle is smaller than the size of the second imaginary triangle.

12. The cell cryopreservation pretreatment operation plate according to claim 10, wherein the first imaginary triangle is located entirely inside the second imaginary triangle.

13. The cell cryopreservation pretreatment operation plate according to claim 10, wherein the first imaginary triangle is located at a central region of the second imaginary triangle.

14. The cell cryopreservation pretreatment operation plate according to claim 10, wherein a portion of the fourth recess completely surrounds at least two of the first recess, the second recess and the third recess.

15. A cell cryopreservation pretreatment operation plate comprising:
- a planar operation portion having an upwardly facing surface;
- a first recess for storing a low-concentration treatment solution that contains a cell membrane-permeable cryoprotectant at a low concentration;
- a second recess for storing a high-concentration treatment solution that contains a cell membrane-permeable cryoprotectant at a high concentration;
- a third recess for storing a high-concentration treatment solution that contains a cell membrane-permeable cryoprotectant at a high concentration;
- a fourth recess for storing a discarded solution;
- the upwardly facing surface of the planar operation portion including three spaced-apart circular segments for placing: i) a cell membrane-permeable cryoprotectant-free treatment solution; ii) the low-concentration treatment solution; and iii) the low-concentration treatment solution;
- the three spaced-apart circular segments including a first circular segment, a second circular segment and a third circular segment;
- the upwardly facing surface of the planar operation portion further including three enlarged first circular segments for placing: i) a cell membrane-permeable cryoprotectant-free treatment solution; ii) the low-concentration treatment solution; and iii) the low-concentration treatment solution;
- the three spaced-apart circular segments including an enlarged first circular segment, an enlarged second circular segment and an enlarged third circular segment;
- the first circular segment, the second circular segment and the third circular segment each having a respective diameter;
- the enlarged first circular segment, the enlarged second circular segment and the enlarged third circular segment each having a respective diameter;
- the diameter of the enlarged first circular segment being larger than the diameter of the first circular segment, the diameter of the enlarged second circular segment being larger than the diameter of the second circular segment, the diameter of the enlarged third circular segment being larger than the diameter of the third circular segment;
- the enlarged first circular segment having an outer edge that is either an annular groove or an annular rib, the enlarged second circular segment having an outer edge that is either an annular groove or an annular rib, and the enlarged third circular segment having an outer edge that is either an annular groove or an annular rib;
- the enlarged first circular segment enclosing the first circular segment, and the first circular segment being in contact with the outer edge of the enlarged first circular segment;
- the enlarged second circular segment enclosing the second circular segment, and the second circular segment being in contact with the outer edge of the enlarged second circular segment; and
- the enlarged third circular segment enclosing the third circular segment.

16. The cell cryopreservation pretreatment operation plate according to claim 15, wherein the third circular segment is in contact with the outer edge of the enlarged third circular segment.

17. The cell cryopreservation pretreatment operation plate according to claim 16, wherein:
- the enlarged first circular segment, the enlarged second circular segment and the enlarged third circular segment each have a respective center;
- the second circular segment contacts the enlarged second circular segment at a second contact point;
- the third circular segment contacts the enlarged third circular segment at a third contact point;
- an inner imaginary triangle connects the first contact point, the second contact point and the third contact point to each other such that a first corner of the inner imaginary triangle is coincident with the first contact point, a second corner of the inner imaginary triangle is coincident with the second contact point, and a third corner of the inner imaginary triangle is coincident with the third contact point;
- an outer imaginary triangle connects the center of the enlarged first circular segment, the center of the second circular segment and the center of the enlarged third circular segment to each other such that a first corner of the outer imaginary triangle is coincident with the center of the enlarged first circular segment, a second corner of the outer imaginary triangle is coincident with the center of the enlarged second circular segment and a third corner of the outer imaginary triangle is coincident with the center of the enlarged third circular segment; and
- the inner imaginary triangle is positioned entirely within the outer imaginary triangle.

18. The cell cryopreservation pretreatment operation plate according to claim 17, wherein:
- the diameter of the enlarged first circular segment is 1.5 to 3 times the diameter of the first circular segment, and an area of the enlarged first circular segment is 2 to 10 times an area of the first circular segment;
- the diameter of the enlarged second circular segment is 1.5 to 3 times the diameter of the second circular segment, and an area of the enlarged second circular segment is 2 to 10 times an area of the second circular segment; and
- the diameter of the enlarged third circular segment is 1.5 to 3 times the diameter of the third circular segment, and an area of the enlarged third circular segment 3 is 2 to 10 times an area of the third circular segment.

* * * * *